US011905544B2

(12) United States Patent
Britton et al.

(10) Patent No.: US 11,905,544 B2
(45) Date of Patent: Feb. 20, 2024

(54) DEHYDRATASE VARIANTS WITH IMPROVED SPECIFIC ACTIVITY FOR THE PRODUCTION OF PYRUVATE FROM GLYCERATE

(71) Applicant: Debut Biotechnology, Inc., San Diego, CA (US)

(72) Inventors: Joshua Britton, San Diego, CA (US); Ali Emileh, San Diego, CA (US)

(73) Assignee: DEBUT BIOTECHNOLOGY, INC., San Diego, CA (US)

( * ) Notice: Subject to any disclaimer, the term of this patent is extended or adjusted under 35 U.S.C. 154(b) by 44 days.

(21) Appl. No.: 17/554,278

(22) Filed: Dec. 17, 2021

(65) Prior Publication Data

US 2022/0195467 A1 Jun. 23, 2022

Related U.S. Application Data

(60) Provisional application No. 63/126,857, filed on Dec. 17, 2020.

(51) Int. Cl.
*C12P 7/40* (2006.01)
*C12N 9/88* (2006.01)
(52) U.S. Cl.
CPC .................. *C12P 7/40* (2013.01); *C12N 9/88* (2013.01); *C12Y 402/01* (2013.01)
(58) Field of Classification Search
CPC .......... C12P 7/40; C12N 9/88; C12Y 402/01; C07K 2319/21
See application file for complete search history.

(56) References Cited

U.S. PATENT DOCUMENTS

| | | | |
|---|---|---|---|
| 6,524,842 | B1 | 2/2003 | Vainberg et al. |
| 10,287,566 | B2 * | 5/2019 | Kelly .................. C12P 7/16 |
| 2009/0239272 | A1 | 9/2009 | Koffas et al. |
| 2010/0081182 | A1 | 4/2010 | Paul et al. |
| 2010/0129886 | A1 | 5/2010 | Anthony et al. |
| 2012/0034661 | A1 | 2/2012 | Stephanopoulos et al. |
| 2014/0273144 | A1 | 9/2014 | Hawkins et al. |
| 2017/0218405 | A1 | 8/2017 | Maggio-Hall et al. |
| 2017/0226497 | A1 | 8/2017 | Kelly et al. |
| 2018/0252713 | A1 | 9/2018 | Weiss et al. |
| 2019/0062768 | A1 | 2/2019 | Ibdah |
| 2020/0080115 | A1 | 3/2020 | Clark et al. |
| 2020/0165558 | A1 | 5/2020 | Shevitz |
| 2020/0255881 | A1 | 8/2020 | Watkins et al. |

FOREIGN PATENT DOCUMENTS

EP 3901256 A1 10/2021

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Sutino et al., Enabling the Direct Enzymatic Dehydration of D-Glycerate to Pyruvate as the Key Step in Synthetic Enzyme Cascades Used in the Cell-Free Production of Fine Chemicals. ACS Catal., 2020, vol. 10: 3110-3118. (Year: 2020).*
Sutino et al., Enabling the Direct Enzymatic Dehydration of D-Glycerate to Pyruvate as the Key Step in Synthetic Enzyme Cascades Used in the Cell-Free Production of Fine Chemicals. ACS Catal., 2020, vol. 10: 3110-3118; supporting information, pp. S1-S18. (Year: 2020).*
Chuck, 2014, Liquid transport fuels from microbial yeasts—current and future perspectives, Biofuels, 5(3):293-311.
Clomburg, 2019, The isoprenoid alcohol pathway, a synthetic route for isoprenoid biosynthesis, PNAS, 116(26):12810-12815.
Degenhardt, 2018, Evaluation of C-prenylating enzymes for the heterologous biosynthesis of cannabigerolic acid, Technical University Dortmund, 180 pages.

(Continued)

*Primary Examiner* — Ganapathirama Raghu
(74) *Attorney, Agent, or Firm* — Brown Rudnick LLP; Adam M. Schoen

(57) ABSTRACT

Glycerol is a byproduct of biodiesel and bioethanol production and its conversion to value-added chemicals is a promising avenue for realization of the biorefinery concept Conversion of glycerol to pyruvate through glycerate yields pyruvate, is a common intermediate of many high-value natural products. The present invention aims at improving the specific activity of a naturally occurring enzyme toward conversion of glycerate to pyruvate (TvDHT). The present invention features compositions of isolated dehydratase enzyme (DHT) polypeptide composition, in particular the DHT polypeptide composition comprising a single point mutation that increases the specific activity of the enzyme as compared to wild type.

17 Claims, 3 Drawing Sheets

Specification includes a Sequence Listing.

(56) References Cited

OTHER PUBLICATIONS

Dudley, 2017, Cell-free Biosynthesis of Isoprenoids using *Escherichia coli* Crude Lysates, Northwestern University, 280 pages.
Gao, 2014, An artificial enzymatic reaction cascade for a cell-free bio-system based on glycerol, Green Chemistry, 2(17):804-807.
International Search Report and Written Opinion issued in International Application No. PCT/US2021/063992, dated Mar. 18, 2022, 9 pages.
International Search Report and Written Opinion issued in International Application No. PCT/US2021/064034, dated Mar. 10, 2022, 11 pages.
International Search Report and Written Opinion issued in International Application No. PCT/US2021/064049, dated Mar. 9, 2022, 8 pages.
Sutiono, 2020, Enabling the Direct Enzymatic Dehydration of D-Glycerate to Pyruvate as the Key Step in Synthetic Enzyme Cascades Used in the Cell-Free Production of Fine Chemicals, ACS Catal, 10(5):3110-3118.
Valliere, 2019, A cell-free platform for the prenylation of natural products and application to cannabinoid production. Nature Communications, 10(565), 9 pages.
Cheng, 2014, Unraveling the mechanism underlying thhe Glycosylation and Methylation of Anthocyanins in Peach, Plant Physiology, 166:1044-1058.
Dudley, 2017, Cell-free Biosynthess of Isoprenoids using *Escherichia coli* Crude Lysates, Nothwestern University, 280 pages.
Gao, 2015, An artificial enzymatic reaction cascade for a cell-free bio-system based on glycerol, Green Chemistry, 2(17):804-807.
International Search Report and Written Opinion issued in International Application No. PCT/US2022/023497, dated Aug. 17, 2022, 17 pages.
International Search Report and Written Opinion issued in International Application No. PCT/US2022/24591, dated Sep. 23, 2022, 26 pages.
Yan, 2005, Metabolic Engineering of Anthocyanin Biosynthesis in *Escherichia coli*, Applied and Environmental Microbiology, 71(7):3617-3623.

* cited by examiner

SEQUENCE LISTING

```
<160> NUMBER OF SEQ ID NOS: 7

<210> SEQ ID NO 1
<211> LENGTH: 560
<212> TYPE: PRT
<213> ORGANISM: Unknown
<220> FEATURE:
<223> OTHER INFORMATION: Thermosynechococcus vulcanus

<400> SEQUENCE: 1

Met Ala Glu Asn Trp Arg Ser Arg Ile Ile Thr Glu Gly Val Gln Arg
1               5                   10                  15

Thr Pro Asn Arg Ala Met Leu Arg Ala Val Gly Phe Gly Asp Glu Asp
            20                  25                  30

Phe Asn Lys Pro Ile Val Gly Val Ala Ser Ala His Ser Thr Ile Thr
        35                  40                  45

Pro Cys Asn Met Gly Ile Ala Ala Leu Ala Ser Arg Ala Glu Ala Gly
    50                  55                  60

Ile Arg Ala Ala Gly Gly Met Pro Gln Leu Phe Gly Thr Ile Thr Val
65                  70                  75                  80

Ser Asp Gly Ile Ser Met Gly Thr Glu Gly Met Lys Tyr Ser Leu Val
                85                  90                  95

Ser Arg Asp Val Ile Ala Asp Ser Ile Glu Thr Val Cys Asn Ala Gln
            100                 105                 110

Ser Met Asp Gly Val Leu Ala Ile Gly Gly Cys Asp Lys Asn Met Pro
        115                 120                 125

Gly Ala Met Ile Ala Met Ala Arg Met Asn Ile Pro Ala Ile Phe Val
    130                 135                 140

Tyr Gly Gly Thr Ile Lys Pro Gly His Trp Gln Gly Gln Asp Leu Thr
145                 150                 155                 160

Val Val Ser Ala Phe Glu Ala Val Gly Gln Phe Ser Ala Gly Lys Met
                165                 170                 175

Asp Glu Ala Thr Leu His Ala Ile Glu His His Ala Cys Pro Gly Ala
            180                 185                 190

Gly Ser Cys Gly Gly Met Phe Thr Ala Asn Thr Met Ser Ser Ala Phe
        195                 200                 205

Glu Ala Met Gly Met Ser Leu Met Tyr Ser Ser Thr Met Thr Ala Glu
    210                 215                 220

Asp Ala Glu Lys Ala Asp Ser Thr Glu Leu Ala Gly Lys Val Leu Val
225                 230                 235                 240

Glu Ala Ile Arg Lys Asn Ile Arg Pro Arg Asp Ile Ile Thr Arg Lys
                245                 250                 255

Ser Ile Glu Asn Ala Ile Ser Val Ile Met Ala Val Gly Gly Ser Thr
            260                 265                 270

Asn Ala Val Leu His Phe Leu Ala Ile Ala His Ser Ala Glu Val Pro
        275                 280                 285
```

Leu Thr Ile Asp Asp Phe Glu Thr Ile Arg Gln Arg Val Pro Val Leu
290                 295                 300

Cys Asp Leu Lys Pro Ser Gly Lys Tyr Val Thr Ala Asp Leu His Arg
305                 310                 315                 320

Ala Gly Gly Ile Pro Gln Val Met Lys Met Leu Leu Asn Ala Gly Leu
            325                 330                 335

Leu His Gly Asp Cys Leu Thr Ile Thr Gly Glu Thr Ile Ala Glu Arg
                340                 345                 350

Leu Arg His Val Pro Asp Thr Pro Asp Pro Asn Gln Asp Val Ile Arg
            355                 360                 365

Pro Phe Asp Gln Pro Leu Tyr Ala Thr Gly His Leu Ala Ile Leu Lys
370                 375                 380

Gly Asn Leu Ala Ser Glu Gly Ala Val Ala Lys Ile Ser Gly Val Lys
385                 390                 395                 400

Asn Pro Gln Ile Thr Gly Pro Ala Arg Val Phe Asp Ser Glu Glu Ala
                405                 410                 415

Cys Leu Asp Ala Ile Leu Ala Gly Lys Ile Asn Pro Gly Asp Val Ile
            420                 425                 430

Val Ile Arg Tyr Glu Gly Pro Val Gly Gly Pro Gly Met Arg Glu Met
            435                 440                 445

Leu Ala Pro Thr Ser Ala Ile Ile Gly Ala Gly Leu Gly Asp Ser Val
450                 455                 460

Gly Leu Ile Thr Asp Gly Arg Phe Ser Gly Gly Thr Tyr Gly Met Val
465                 470                 475                 480

Val Gly His Val Ala Pro Glu Ala Ala Val Gly Gly Thr Ile Ala Leu
                485                 490                 495

Val Gln Glu Gly Asp Ser Ile Thr Ile Asp Ala His Arg Arg Leu Leu
            500                 505                 510

Gln Leu Asn Val Ser Glu Glu Leu Ala Ala Arg Arg Ala Lys Trp
            515                 520                 525

Gln Pro Pro Ala Pro Arg Tyr Thr Arg Gly Val Leu Ala Lys Tyr Ala
530                 535                 540

Lys Leu Val Ser Ser Ser Ser Leu Gly Ala Val Thr Asp Arg Phe Val
545                 550                 555                 560

<210> SEQ ID NO 2
<211> LENGTH: 1679
<212> TYPE: DNA
<213> ORGANISM: Unknown
<220> FEATURE:
<223> OTHER INFORMATION: Codon-optimized TvDHT nucleotide sequence

<400> SEQUENCE: 2
tggccgagaa ttggcgtagt cgtattatta ccgagggcgt gcaacgtacg ccgaatcgcg    60
caatgctgcg tgcagttggg ttcggtgacg aggacttcaa caagccgatt gtcggcgtgg   120
ccagcgccca ctcgactatt accccttgta atatgggat gcggcgttg gcctcgcgtg    180 ccgaggcggg tattcgtgcg gcgggtggta tgccgcaact gttcggaacg atcacagtct   240
ctgatggcat tagcatggga accgagggaa tgaagtatag tctggtgagc cgtgatgtca   300
tcgctgatag cattgagact gtttgtaacg cccagtctat ggatggcgtt ttggcgatcg   360
gtggctgtga taagaacatg ccgggagcga tgatcgcaat ggcgcgtatg aatattccgg   420
cgattttcgt gtacggtggg accatcaagc tgggcattg gcaggtcag gatttaactg    480 tggtatccgc gttcgaggca gtgggtcaat tcagcgcggg taaaatggat gaagcgactc   540

| | |
|---|---|
| tccacgcgat tgagcaccac gcctgccccg gggcgggctc ttgcggcggt atgttcacag | 600 |
| ctaacacgat gagttccgca ttcgaggcca tgggcatgtc gttgatgtat agctcgacaa | 660 |
| tgaccgccga agacgcggag aaggccgata gcaccgaact ggctggtaag gtgctcgtgg | 720 |
| aagcgattcg taagaatatt cgtccccgtg acattatcac gcgcaagtca atcgaaaacg | 780 |
| caatctccgt gattatggct gtcggcggtt ccaccaacgc cgtccttcac ttcctggcga | 840 |
| tcgcccattc agcagaagta cctttaacca tcgacgactt tgagacgatt cgccagcgcg | 900 |
| tcccagtgtt atgcgatttg aagccatcgg ggaagtatgt caccgccgac ctgcaccgtg | 960 |
| ctggcggcat cccgcaagtg atgaaaatgc tcttaaatgc cggcctgttg catggtgact | 1020 |
| gcttaaccat caccggggag actattgcag agcgcttacg ccacgtcccg gataccccgg | 1080 |
| atccgaatca agacgtaatc cgccccttg accaaccgtt atatgccaca gggcacctgg | 1140 |
| ccattctgaa aggaaacctg gcatccgaag gggcggttgc taagatcagc ggcgtgaaga | 1200 |
| atcctcaaat tacggggccg gcacgcgtat cgacagcga agaggcatgc ttggacgcca | 1260 |
| tcttggctgg caaaattaac cctggtgacg ttattgttat tcgctacgaa ggtccggtgg | 1320 |
| gcggcccagg gatgcgcgag atgctggccc ccacatctgc catcattggt gccgggttag | 1380 |
| gggatagtgt tggactgatt acagatgggc gcttttcggg tggtacttat ggtatggtgg | 1440 |
| tgggccatgt tgcaccggaa gcggccgtgg gtggaaccat cgcgcttgtc caagagggcg | 1500 |
| actctattac tatcgatgct caccgccgtc tgcttcagct gaatgtatca gaagaggagt | 1560 |
| tagcggcgcg ccgcgccaag tggcaaccac cggcccctcg ctacactcgt ggtgttttgg | 1620 |
| cgaagtatgc caagctcgtt agctcgagca gcttgggtgc cgttacggac cgtttcgtg | 1679 |

<210> SEQ ID NO 3
<211> LENGTH: 1679
<212> TYPE: DNA
<213> ORGANISM: Unknown
<220> FEATURE:
<223> OTHER INFORMATION: TvDHT - B7 (L95I) nucleotide sequence

<400> SEQUENCE: 3

| | |
|---|---|
| tggccgagaa ttggcgtagt cgtattatta ccgagggcgt gcaacgtacg ccgaatcgcg | 60 |
| caatgctgcg tgcagttggg ttcggtgacg aggacttcaa caagccgatt gtcggcgtgg | 120 |
| ccagcgccca ctcgactatt accccttgta atatggggat tgcggcgttg gcctcgcgtg | 180 |
| ccgaggcggg tattcgtgcg gcgggtggta tgccgcaact gttcggaacg atcacagtct | 240 |
| ctgatggcat tagcatggga accgagggaa tgaagtatag tatttgtgagc cgtgatgtca | 300 |
| tcgctgatag cattgagact gtttgtaacg cccagtctat ggatggcgtt ttggcgatcg | 360 |
| gtggctgtga taagaacatg ccgggagcga tgatcgcaat ggcgcgtatg aatattccgg | 420 |
| cgattttcgt gtacggtggg accatcaagc ctgggcattg gcagggtcag gatttaactg | 480 |
| tggtatccgc gttcgaggca gtgggtcaat tcagcgcggg taaaatggat gaagcgactc | 540 |
| tccacgcgat tgagcaccac gcctgccccg gggcgggctc ttgcggcggt atgttcacag | 600 |
| ctaacacgat gagttccgca ttcgaggcca tgggcatgtc gttgatgtat agctcgacaa | 660 |
| tgaccgccga agacgcggag aaggccgata gcaccgaact ggctggtaag gtgctcgtgg | 720 |
| aagcgattcg taagaatatt cgtccccgtg acattatcac gcgcaagtca atcgaaaacg | 780 |
| caatctccgt gattatggct gtcggcggtt ccaccaacgc cgtccttcac ttcctggcga | 840 |
| tcgcccattc agcagaagta cctttaacca tcgacgactt tgagacgatt cgccagcgcg | 900 |
| tcccagtgtt atgcgatttg aagccatcgg ggaagtatgt caccgccgac ctgcaccgtg | 960 |

-continued

```
ctggcggcat cccgcaagtg atgaaaatgc tcttaaatgc cggcctgttg catggtgact    1020
gcttaaccat caccggggag actattgcag agcgcttacg ccacgtcccg datacccgg     1080 atccgaatca agacgtaatc cgccccttg accaaccgtt atatgccaca gggcacctgg     1140
ccattctgaa aggaaacctg gcatccgaag ggcggttgc taagatcagc ggcgtgaaga     1200
atcctcaaat tacggggccg gcacgcgtat tcgacagcga agaggcatgc ttggacgcca    1260
tcttggctgg caaaattaac cctggtgacg ttattgttat tcgctacgaa ggtccggtgg    1320
gcggcccagg gatgcgcgag atgctggccc ccacatctgc catcattggt gccgggttag    1380
gggatagtgt tggactgatt acagatgggc gcttttcggg tggtacttat ggtatggtgg    1440
tgggccatgt tgcaccggaa gcggccgtgg gtggaaccat cgcgcttgtc caagagggcg    1500
actctattac tatcgatgct caccgccgtc tgcttcagct gaatgtatca agagaggagt    1560
tagcggcgcg ccgcgccaag tgcaaccac cggcccctcg ctacactcgt ggtgttttgg     1620
cgaagtatgc caagctcgtt agctcgagca gcttgggtgc cgttacggac cgtttcgtg    1679
```

<210> SEQ ID NO 4
<211> LENGTH: 560
<212> TYPE: PRT
<213> ORGANISM: Unknown
<220> FEATURE:
<223> OTHER INFORMATION: TvDHT - B7 (L95I) amino acid sequence

<400> SEQUENCE: 4

```
Met Ala Glu Asn Trp Arg Ser Arg Ile Ile Thr Glu Gly Val Gln Arg
1               5                   10                  15

Thr Pro Asn Arg Ala Met Leu Arg Ala Val Gly Phe Gly Asp Glu Asp
            20                  25                  30

Phe Asn Lys Pro Ile Val Gly Val Ala Ser Ala His Ser Thr Ile Thr
        35                  40                  45

Pro Cys Asn Met Gly Ile Ala Ala Leu Ala Ser Arg Ala Glu Ala Gly
    50                  55                  60

Ile Arg Ala Ala Gly Gly Met Pro Gln Leu Phe Gly Thr Ile Thr Val
65                  70                  75                  80

Ser Asp Gly Ile Ser Met Gly Thr Glu Gly Met Lys Tyr Ser Ile Val
                85                  90                  95

Ser Arg Asp Val Ile Ala Asp Ser Ile Glu Thr Val Cys Asn Ala Gln
            100                 105                 110

Ser Met Asp Gly Val Leu Ala Ile Gly Gly Cys Asp Lys Asn Met Pro
        115                 120                 125

Gly Ala Met Ile Ala Met Ala Arg Met Asn Ile Pro Ala Ile Phe Val
    130                 135                 140

Tyr Gly Gly Thr Ile Lys Pro Gly His Trp Gln Gly Gln Asp Leu Thr
145                 150                 155                 160

Val Val Ser Ala Phe Glu Ala Val Gly Gln Phe Ser Ala Gly Lys Met
                165                 170                 175

Asp Glu Ala Thr Leu His Ala Ile Glu His His Ala Cys Pro Gly Ala
            180                 185                 190

Gly Ser Cys Gly Gly Met Phe Thr Ala Asn Thr Met Ser Ser Ala Phe
        195                 200                 205

Glu Ala Met Gly Met Ser Leu Met Tyr Ser Ser Thr Met Thr Ala Glu
    210                 215                 220

Asp Ala Glu Lys Ala Asp Ser Thr Glu Leu Ala Gly Lys Val Leu Val
225                 230                 235                 240
```

Glu Ala Ile Arg Lys Asn Ile Arg Pro Arg Asp Ile Ile Thr Arg Lys
            245                 250                 255

Ser Ile Glu Asn Ala Ile Ser Val Ile Met Ala Val Gly Gly Ser Thr
            260                 265                 270

Asn Ala Val Leu His Phe Leu Ala Ile Ala His Ser Ala Glu Val Pro
            275                 280                 285

Leu Thr Ile Asp Asp Phe Glu Thr Ile Arg Gln Arg Val Pro Val Leu
            290                 295                 300

Cys Asp Leu Lys Pro Ser Gly Lys Tyr Val Thr Ala Asp Leu His Arg
305                 310                 315                 320

Ala Gly Gly Ile Pro Gln Val Met Lys Met Leu Leu Asn Ala Gly Leu
                325                 330                 335

Leu His Gly Asp Cys Leu Thr Ile Thr Gly Glu Thr Ile Ala Glu Arg
                340                 345                 350

Leu Arg His Val Pro Asp Thr Pro Asp Pro Asn Gln Asp Val Ile Arg
                355                 360                 365

Pro Phe Asp Gln Pro Leu Tyr Ala Thr Gly His Leu Ala Ile Leu Lys
370                 375                 380

Gly Asn Leu Ala Ser Glu Gly Ala Val Ala Lys Ile Ser Gly Val Lys
385                 390                 395                 400

Asn Pro Gln Ile Thr Gly Pro Ala Arg Val Phe Asp Ser Glu Glu Ala
                405                 410                 415

Cys Leu Asp Ala Ile Leu Ala Gly Lys Ile Asn Pro Gly Asp Val Ile
                420                 425                 430

Val Ile Arg Tyr Glu Gly Pro Val Gly Gly Pro Gly Met Arg Glu Met
                435                 440                 445

Leu Ala Pro Thr Ser Ala Ile Ile Gly Ala Gly Leu Gly Asp Ser Val
            450                 455                 460

Gly Leu Ile Thr Asp Gly Arg Phe Ser Gly Thr Tyr Gly Met Val
465                 470                 475                 480

Val Gly His Val Ala Pro Glu Ala Ala Val Gly Gly Thr Ile Ala Leu
                485                 490                 495

Val Gln Glu Gly Asp Ser Ile Thr Ile Asp Ala His Arg Arg Leu Leu
                500                 505                 510

Gln Leu Asn Val Ser Glu Glu Leu Ala Ala Arg Arg Ala Lys Trp
            515                 520                 525

Gln Pro Pro Ala Pro Arg Tyr Thr Arg Gly Val Leu Ala Lys Tyr Ala
530                 535                 540

Lys Leu Val Ser Ser Ser Ser Leu Gly Ala Val Thr Asp Arg Phe Val
545                 550                 555                 560

<210> SEQ ID NO 5
<211> LENGTH: 1680
<212> TYPE: DNA
<213> ORGANISM: Unknown
<220> FEATURE:
<223> OTHER INFORMATION: TvDHT - G8 (V96F) nucleotide sequence

<400> SEQUENCE: 5
atggccgaga attggcgtag tcgtattatt accgagggcg tgcaacgtac gccgaatcgc        60
gcaatgctgc gtgcagttgg gttcggtgac gaggacttca acaagccgat tgtcggcgtg       120
gccagcgccc actcgactat taccccttgt aatatgggga ttgcggcgtt ggcctcgcgt       180
gccgaggcgg gtattcgtgc ggcgggtggt atgccgcaac tgttcggaac gatcacagtc       240

```
tctgatggca ttagcatggg aaccgaggga atgaagtata gtctgtttag ccgtgatgtc    300
atcgctgata gcattgagac tgtttgtaac gcccagtcta tggatggcgt tttggcgatc    360
ggtggctgtg ataagaacat gccgggagcg atgatcgcaa tggcgcgtat gaatattccg    420
gcgattttcg tgtacggtgg gaccatcaag cctgggcatt ggcagggtca ggatttaact    480
gtggtatccg cgttcgaggc agtgggtcaa ttcagcgcgg gtaaaatgga tgaagcgact    540
ctccacgcga ttgagcacca cgcctgcccc ggggcgggct cttgcggcgg tatgttcaca    600
gctaacacga tgagttccgc attcgaggcc atgggcatgt cgttgatgta tagctcgaca    660
atgaccgccg aagacgcgga gaaggccgat agcaccgaac tggctggtaa ggtgctcgtg    720
gaagcgattc gtaagaatat tcgtccccgt gacattatca cgcgcaagtc aatcgaaaac    780
gcaatctccg tgattatggc tgtcggcggt tccaccaacg ccgtccttca cttcctggcg    840
atcgcccatt cagcagaagt acctttaacc atcgacgact ttgagacgat tcgccagcgc    900
gtcccagtgt tatgcgattt gaagccatcg gggaagtatg tcaccgccga cctgcaccgt    960
gctggcggca tcccgcaagt gatgaaaatg ctcttaaatg ccggcctgtt gcatggtgac   1020
tgcttaacca tcaccgggga gactattgca gagcgcttac gccacgtccc ggatacccg    1080 gatccgaatc aagacgtaat ccgccccttt gaccaaccgt tatatgccac agggcacctg   1140
gccattctga aggaaacct ggcatccgaa ggggcggttg ctaagatcag cggcgtgaag    1200
aatcctcaaa ttacggggcc ggcacgcgta ttcgacagcg aagaggcatg cttggacgcc   1260
atcttggctg caaaattaa ccctggtgac gttattgtta ttcgctacga aggtccggtg   1320
ggcggcccag ggatgcgcga gatgctggcc cccacatctg ccatcattgg tgccgggtta   1380
ggggatagtg ttggactgat tacagatggg cgcttttcgg gtggtactta tggtatggtg   1440
gtgggccatg ttgcaccgga agcggccgtg ggtggaacca tcgcgcttgt ccaagagggc   1500
gactctatta ctatcgatgc tcaccgccgt ctgcttcagc tgaatgtatc agaagaggag   1560
ttagcggcgc gccgcgccaa gtggcaacca ccggccccto gctacactcg tggtgttttg   1620
gcgaagtatg ccaagctcgt tagctcgagc agcttgggtg ccgttacgga ccgtttcgtg   1680
```

<210> SEQ ID NO 6
<211> LENGTH: 559
<212> TYPE: PRT
<213> ORGANISM: Unknown
<220> FEATURE:
<223> OTHER INFORMATION: TvDHT - G8 (V96F) amino acid sequence

<400> SEQUENCE: 6

Met Ala Glu Asn Trp Arg Ser Arg Ile Ile Thr Glu Gly Val Gln Arg
1               5                   10                  15

Thr Pro Asn Arg Ala Met Leu Arg Ala Val Gly Phe Gly Asp Glu Asp
            20                  25                  30

Phe Asn Lys Pro Ile Val Gly Val Ala Ser Ala His Ser Thr Ile Thr
        35                  40                  45

Pro Cys Asn Met Gly Ile Ala Ala Leu Ala Ser Arg Ala Glu Ala Gly
    50                  55                  60

Ile Arg Ala Ala Gly Gly Met Pro Gln Leu Phe Gly Thr Ile Thr Val
65                  70                  75                  80

Ser Asp Gly Ile Ser Met Gly Thr Glu Gly Met Lys Tyr Ser Leu Phe
                85                  90                  95

Ser Arg Asp Val Ile Ala Asp Ser Ile Glu Thr Val Cys Asn Ala Gln
            100                 105                 110

-continued

```
Ser Met Asp Gly Val Leu Ala Ile Gly Gly Cys Asp Lys Asn Met Pro
            115                 120                 125
Gly Ala Met Ile Ala Met Ala Arg Met Asn Ile Pro Ala Ile Phe Val
130                 135                 140
Tyr Gly Thr Ile Lys Pro Gly His Trp Gln Gly Gln Asp Leu Thr
145                 150                 155                 160
Val Val Ser Ala Phe Glu Ala Val Gly Gln Phe Ser Ala Gly Lys Met
                165                 170                 175
Asp Glu Ala Thr Leu His Ala Ile Glu His His Ala Cys Pro Gly Ala
            180                 185                 190
Gly Ser Cys Gly Gly Met Phe Thr Ala Asn Thr Met Ser Ser Ala Phe
        195                 200                 205
Glu Ala Met Gly Met Ser Leu Met Tyr Ser Ser Thr Met Thr Ala Glu
210                 215                 220
Asp Ala Glu Lys Ala Asp Ser Thr Glu Leu Ala Gly Lys Val Leu Val
225                 230                 235                 240
Glu Ala Ile Arg Lys Asn Ile Arg Pro Arg Asp Ile Ile Thr Arg Lys
                245                 250                 255
Ser Ile Glu Asn Ala Ile Ser Val Ile Met Ala Val Gly Gly Ser Thr
            260                 265                 270
Asn Ala Val Leu His Phe Leu Ala Ile Ala His Ser Ala Glu Val Pro
        275                 280                 285
Leu Thr Ile Asp Asp Phe Glu Thr Ile Arg Gln Arg Val Pro Val Leu
    290                 295                 300
Cys Asp Leu Lys Pro Ser Gly Lys Tyr Val Thr Ala Asp Leu His Arg
305                 310                 315                 320
Ala Gly Gly Ile Pro Gln Val Met Lys Met Leu Leu Asn Ala Gly Leu
                325                 330                 335
Leu His Gly Asp Cys Leu Thr Ile Thr Gly Glu Thr Ile Ala Glu Arg
            340                 345                 350
Leu Arg His Val Pro Asp Thr Pro Asp Pro Asn Gln Asp Val Ile Arg
        355                 360                 365
Pro Phe Asp Gln Pro Leu Tyr Ala Thr Gly His Leu Ala Ile Leu Lys
    370                 375                 380
Gly Asn Leu Ala Ser Glu Gly Ala Val Ala Lys Ile Ser Gly Val Lys
385                 390                 395                 400
Asn Pro Gln Ile Thr Gly Pro Ala Arg Val Phe Asp Ser Glu Glu Ala
                405                 410                 415
Cys Leu Asp Ala Ile Leu Ala Gly Lys Ile Asn Pro Gly Asp Val Ile
            420                 425                 430
Val Ile Arg Tyr Glu Gly Pro Val Gly Gly Pro Gly Met Arg Glu Met
        435                 440                 445
Leu Ala Pro Thr Ser Ala Ile Ile Gly Ala Gly Leu Gly Asp Ser Val
    450                 455                 460
Gly Leu Ile Thr Asp Gly Arg Phe Ser Gly Gly Thr Tyr Gly Met Val
465                 470                 475                 480
Val Gly His Val Ala Pro Glu Ala Ala Val Gly Gly Thr Ile Ala Leu
                485                 490                 495
Val Gln Glu Gly Asp Ser Ile Thr Ile Asp Ala His Arg Arg Leu Leu
            500                 505                 510
Gln Leu Asn Val Ser Glu Glu Leu Ala Ala Arg Arg Ala Lys Trp
        515                 520                 525
Gln Pro Pro Ala Pro Arg Tyr Thr Arg Gly Val Leu Ala Lys Tyr Ala
```

```
                530              535              540
Lys Leu Val Ser Ser Ser Leu Gly Ala Val Thr Asp Arg Phe
545                  550              555

<210> SEQ ID NO 7
<211> LENGTH: 20
<212> TYPE: DNA
<213> ORGANISM: Unknown
<220> FEATURE:
<223> OTHER INFORMATION: T7 primer

<400> SEQUENCE: 7
taatacgact cactataggg                                      20
```

DEHYDRATASE VARIANTS WITH IMPROVED SPECIFIC ACTIVITY FOR THE PRODUCTION OF PYRUVATE FROM GLYCERATE

CROSS-REFERENCES TO RELATED APPLICATIONS

This application is a non-provisional and claims benefit of U.S. Provisional Application No. 63/126,857 filed Dec. 17, 2020, the specification of which is incorporated herein in their entirety by reference.

REFERENCE TO A SEQUENCE LISTING

Applicant asserts that the paper copy of the Sequence Listing is identical to the Sequence Listing in computer readable form found on the accompanying computer file, entitled DEBUT_20_02_NP_Sequence_Listing_ST25. The content of the sequence listing is incorporated herein by reference in its entirety.

FIELD OF THE INVENTION

The present invention features compositions of isolated dehydratase enzyme (DHT) polypeptide composition, in particular the DHT polypeptide composition comprising a single point mutation that increases the specific activity of the enzyme as compared to wild type.

BACKGROUND OF THE INVENTION

Glycerol is a byproduct of biodiesel and bioethanol production and its conversion to value-added chemicals is a promising avenue for realization of the biorefinery concept. While microbial production of chemicals using glycerol have advanced significantly, issues with substrate toxicity, product and substrate availability, and operational complexities, have prevented wider adoption of such approaches. Cell-free approaches (using enzymes found in cellular pathways in vitro) have attracted attention in recent years due to their ability to overcome the above limitations.

Cell-free bioconversion of glycerol into pyruvic acid via glycolysis involves expensive cofactors like NADH and ATP, making this approach economically unattractive. An alternative enzymatic cascade to create pyruvic acid is now available that simplifies glycolysis while removing the need for expensive cofactors. Not only is pyruvic acid a product of glycolysis, but this molecule is an important building block for biosynthesis of many chemicals, pharmaceuticals, and food additives (FIG. 1). For the biosynthesis of pyruvic acid, DHAD (dihydroxy acid dehydratase) enzyme from *S. solfataricus* (SsDHAD) can be used to construct a synthetic cascade, but this has been identified as a bottleneck for efficient conversion of glycerol to pyruvate, and efforts to improve the enzyme specific activity have not yet yielded significantly improved variants. However, a new class of dehydratase enzymes (DHTs) were discovered that could catalyze glycerate conversion into pyruvic acid more efficiently.

As a waste stream of biodiesel manufacturing, glycerol is an ideal low value starting material for use in such applications. Conversion of glycerol to pyruvate through glycerate yields pyruvate, a common intermediate of many high-value natural products. The present invention aims at improving the specific activity of a naturally occurring enzyme toward conversion of glycerate to pyruvate (TvDHT).

BRIEF SUMMARY OF THE INVENTION

It is an objective of the present invention to provide compositions with single point mutations that allows for a dehydratase enzyme (DHT) that has an increase in specific activity toward glyceric acid compared to the wild type protein, as specified in the independent claims. Embodiments of the invention are given in the dependent claims. Embodiments of the present invention can be freely combined with each other if they are not mutually exclusive.

In some embodiments, the present invention features an isolated dehydratase enzyme (DHT) polypeptide comprising at least a single point mutation. In some embodiments, the point mutation increases specific activity of the DHT polypeptide compared to a wild type DHT protein. In some embodiments, the point mutation is L95I. In other embodiments, the point mutation is V96F.

In other embodiments, the present invention features an isolated dehydratase enzyme (DHT) polypeptide composition comprising a sequence that is at least 90% identical to SEQ ID NO: 4 or SEQ ID NO: 6 (Table 1).

One of the unique and inventive technical features of the present invention is a dehydratase enzyme (DHT) polypeptide composition that comprises a single point mutation. Without wishing to limit the invention to any theory or mechanism, it is believed that the technical feature of the present invention advantageously provides for the creation of DHT variants that increase the specific activity of the enzyme towards glyceric acid by two to seven-fold. None of the presently known prior references or work has the unique inventive technical feature of the present invention.

Furthermore, the prior references teach away from the present invention. For example, Begander et al. attempted to engineer an improved variant of *Sulfolobus solfataricus* D-glycerate dehydratase (SsDHAD), toward glycerate conversion to pyruvate (see FIG. 1). Despite best efforts, large variations had to be accepted in the assay signal possibly due to presence of endogenous proteins and small molecules. As the product of this enzyme reaction (pyruvate) is a key chemical in cell metabolism, not only pyruvate levels inside the cell are different between individual cells but they can continue to change after cell lysis due to the presence of endogenous enzymes in the lysate. Therefore, presence of endogenous enzymes and pyruvate in the assay is expected to increase assay variability. To avoid such problems and to establish a screen with lower noise levels, the present invention developed a robotic high-throughput purification platform which allowed us to purify the enzymes of interest out of the bacterial lysate. This strategy not only removed the interfering endogenous proteins and small molecules (like pyruvate), but it also enabled protein concentration quantification using ELISA (which displayed high noise levels with crude lysate); Begander et al. did not measure protein concentrations in their initial screen, which may explain their low success rate in follow-up screening (2 out of 65 primary hits were confirmed).

Additionally, single mutations can change protein expression levels significantly, and that in turn can impact the activity signal observed in a screen. Therefore, normalization of the activity signal to enzyme concentration is necessary to select candidates which show the most increase in specific activity. It is the latter quantity which will eventually determine superiority of a mutant over WT, as it dictates the amount of enzyme needed to reach a certain activity level, in turn determining the cost of enzyme in a biocatalysis process.

Finally, the fluorescent dye used by Begander et al. was susceptible to reduction back to the non-fluorescent state, but there are no reports of such issues for the dye used in the screen described herein. Use of Amplex red in the present screen along with high throughput purification most likely abrogated any similar possible problems. In conclusion, the use of high-throughput robotic purification, enzyme concentration determination and activity normalization using this data, along with the use of a more robust fluorescent dye separates the present screening approach from that used by Begander et al. and possibly contributed to the higher screening hit rate of the present invention (2 confirmed hits from 360 clones, compared to 1 from 1200 in Begander et al.).

Furthermore, the inventive technical features of the present invention contributed to a surprising result. When initially designing the variant library, it was hypothesized that limiting the library diversity to the set of DHT backbones disclosed by Sutiono et al. will increase the possibility that the mutants will fold properly and be active. Such a focused design of libraries by learning from nature has been shown to increase library quality, while decreasing screening effort. Nonetheless, some random mutations were included in the library to hedge against excessive limitation of library diversity. This was achieved by selecting the threshold for acceptance of log-likelihood values in a position-specific scoring matrix (PSSM) built from this limited set of sequences to a value that would allow for some random mutations. The library size was further limited by focusing the diversity to regions of the TvDHT sequence that were expected to impact activity, based on 3D models of the structure generated. Surprisingly, both of the presently claimed improved mutants came from these random mutations, and not from those expected based on the amino acid sequence of the set disclosed by Sutiono et al.

In total, there are 10,640 possible single-point mutations within TvDHT sequence, and it is not a priori obvious which ones can lead to an improved mutant. Using a reduced amino acid alphabet based on natural sequences, while allowing for some random mutations, a focused mutant library was designed which significantly reduced library size and required much less screening effort. This allowed for the discovery of two (2) mutants which individually could improve specific activity by at least 5-fold by screening only 360 colonies, compared to 1200 colonies in the only comparable report in the literature. In conclusion, while the approach was based on natural diversity, the resulting improved mutants were surprisingly not observed in nature, and this lends support to the initial decision to include some randomness in the design of the library.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

Figure 5:
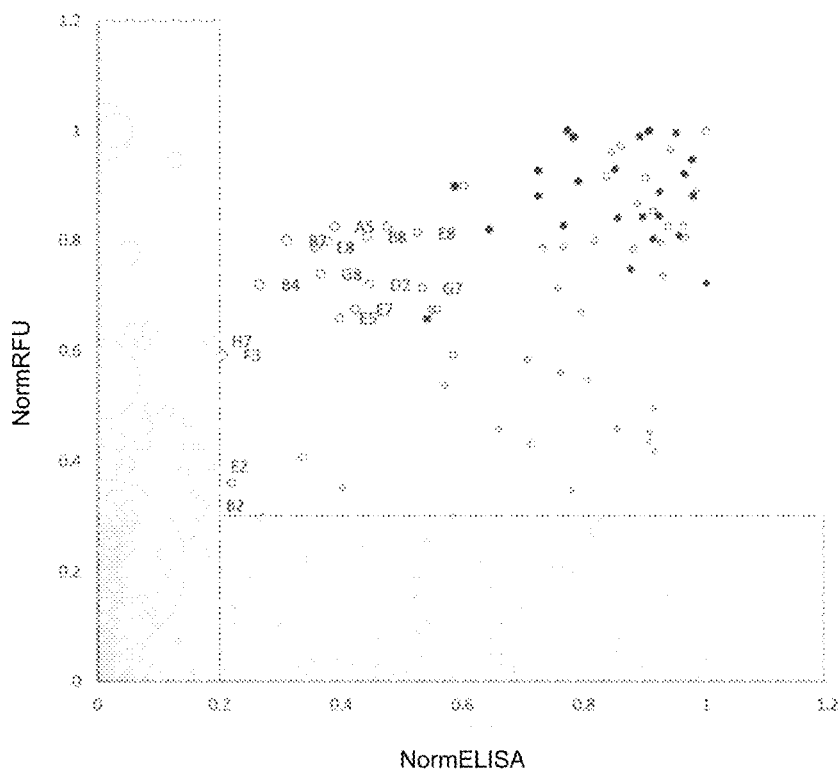
Figure 6:
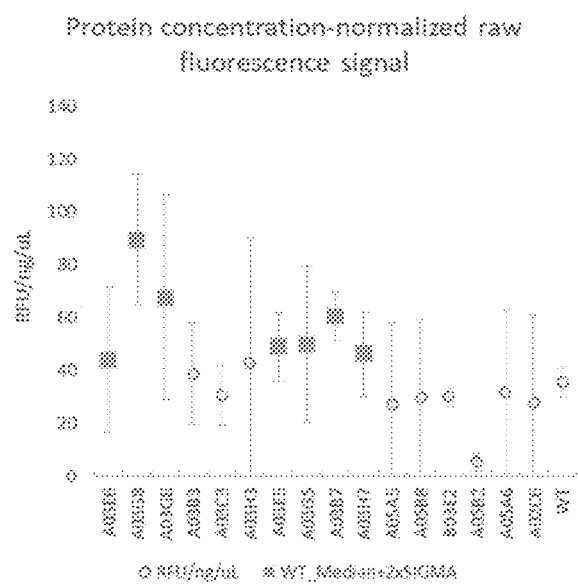

FIG. 5 shows a normalized assay signal (NormRFU) plotted against normalized ELISA signal (NormELISA), for a representative set of samples, at 800× dilution. Width of circles denotes normalized ENS (expression normalized signal). Open circles are variants, and filled circles are WT. Identified hits among this cohort are labeled. The shaded area approximately shows the regions where the implemented filters would reject samples FIG. 6 shows the activity signal normalized to protein concentration for the final set of variants expressed in 24-well deep well plates. Squares are variants where the signal is two standard deviations above that of the WT median. Measurements are done in quadruplicate, and for WT, with 4 biological replicates, unless a measurement fails to pass the filters (see below).

Figure 7:
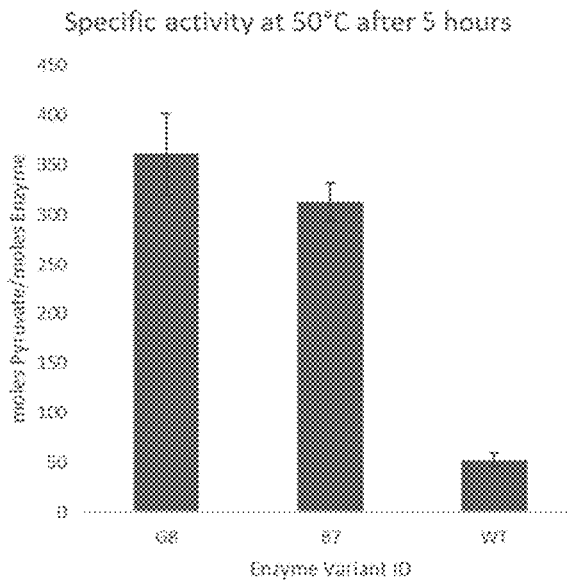

FIG. 7 shows the specific activity of the final variants measured at 50° C. and after five hours. Concentrations were measured using ELISA. Error bars correspond to concentration measurement standard deviations (n=3).

Figure 8:
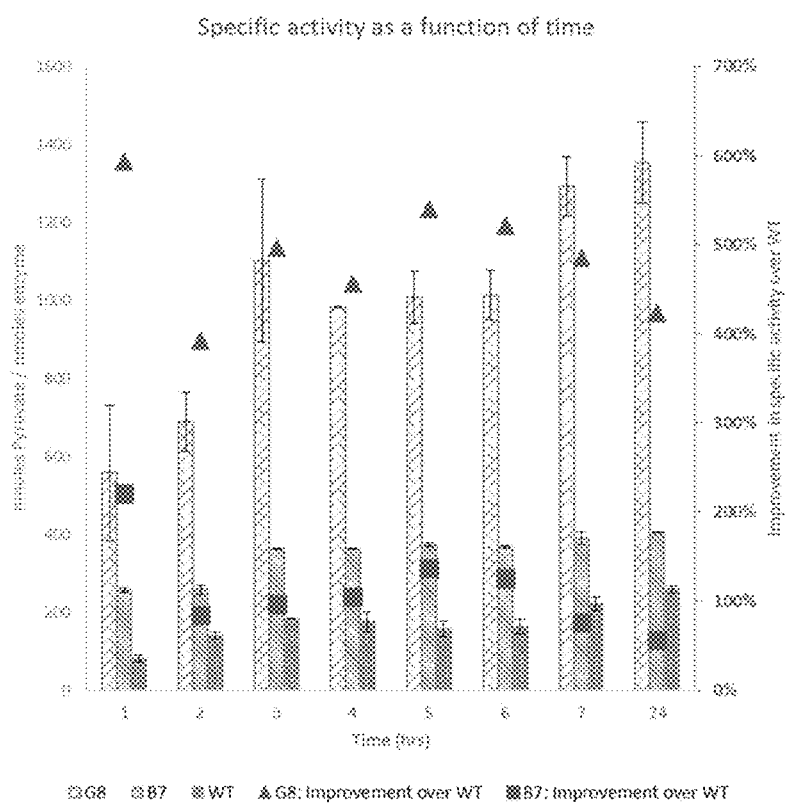

FIG. 8 shows the specific activity of the new variants and the WT as a function of time. Pyruvate concentrations were measured via HPLC (n=2). Enzyme concentrations were measured via ELISA (n=3). Error bars represent the standard deviation of individually derived specific activity values. The right y-axis shows the percent improvement in specific activity when compared to WT at the same time point.

DETAILED DESCRIPTION OF THE INVENTION

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

As used herein "wild type" refers to a gene when it is found in its natural, non-mutated (unchanged) form. "Wild type", "WT", and "Wild type backbone" may be used interchangeably. As used herein the TvDHT (SEQ. ID. NO. 1) was chosen as the starting sequence and is referred to as the wild type. In some embodiments, SEQ ID NO. 2 is the DNA sequence from which SEQ ID NO. 1 is translated.

As used herein "variant" or "mutant" may be used interchangeably and may refer to a specific region of a sequence which differs between two genes.

As used herein, the term "variant" refers to a substantially similar sequence. For polynucleotides, a variant comprises a deletion and/or addition and/or change of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or an amino acid sequence, respectively. "Variant" protein is intended to mean a protein derived from the native protein by deletion or addition of one or more amino acids at one or more sites in the native protein and/or substitution (i.e., a point mutation) of one or more amino acids at one or more sites in the native protein. Variant proteins encompassed by the present disclosure are biologically active (i.e., can convert glycerate to pyruvate).

As used herein "specific activity" refers to the activity per unit of enzyme mass.

Referring now to FIGS. 1-8, the present invention features an isolated dehydratase enzyme (DHT) polypeptide composition comprising a sequence that is at least 90% identical to SEQ ID NO: 4 or SEQ ID NO: 6 (Table 1).

TABLE 1

| Name | Sequence: | SEQ ID NO: |
|---|---|---|
| TvDHAD_WP_126985616.1 dihydroxy-acid dehydratase [*Thermosynechococcus vulcanus*] | MAENWRSRIITEGVQRTPNRAMLRAVGFGDEDFNKPIVGVASAHSTITP CNMGIAALASRAEAGIRAAGGMPQLFGTITVSDGISMGTEGMKYSLVSR DVIADSIETVCNAQSMDGVLAIGGCDKNMPGAMIAMARMNIPAIFVYGGT IKPGHWQGQDLTVVSAFEAVGQFSAGKMDEATLHAIEHHACPGAGSCG GMFTANTMSSAFEAMGMSLMYSSTMTAEDAEKADSTELAGKVLVEAIR KNIRPRDIITRKSIENAISVIMAVGGSTNAVLHFLAIAHSAEVPLTIDDFETIR QRVPVLCDLKPSGKYVTADLHRAGGIPQVMKMLLNAGLLHGDCLTITGE TIAERLRHVPDTPDPNQDVIRPFDQPLYATGHLAILKGNLASEGAVAKISG VKNPQITGPARVFDSEEACLDAILAGKINPGDVIVIRYEGPVGGPGMREM LAPTSAIIGAGLGDSVGLITDGRFSGGTYGMVVGHVAPEAAVGGTIALVQ EGDSITIDAHRRLLQLNVSEEELAARRAKWQPPAPRYTRGVLAKYAKLV SSSSLGAVTDRFV | 1 |
| Codon-optimized TvDHT nucleotide sequence | tggccgagaattggcgtagtcgtattattaccgagggcgtgcaacgtacgccgaatcgcgca atgctgcgtgcagttgggttcggtgacgaggacttcaacaagccgattgtcggcgtggccag cgcccactcgactattaccccttgtaatatggggattgcggcgttggcctcgcgtgccgaggc gggtattcgtgcggcgggtggtatgccgcaactgttcggaacgatcacagtctctgatggcat tagcatgggaaccgagggaatgaagtatagtatctggtgagccgtgatgtcatcgctgatagca ttgagactgtttgtaacgcccagtctatggatggcgttttggcgatcggtggctgtgataagaac atgccgggagcgatgatcgcaatggcgcgtatgaatattccggcgattttcgtgtacggtggg accatcaagcctgggcattggcagggtcaggatttaactgtggtatccgcgttcgaggcagt gggtcaattcagcgcgggtaaaatggatgaagcgactctccacgcgattgagcaccacgc ctgccccggggcgggctcttgcggcggtatgttcacagctaacacgatgagttccgcattcg aggccatgggcatgtcgttgatgtatagctcgacaatgaccgccgaagacgcggagaagg ccgatagcaccgaactggctggtaaggtgctcgtggaagcgattcgtaagaatattcgtccc cgtgacattatcacgcgcaagtcaatcgaaaacgcaatctccgtgattatggctgtcggcggt tccaccaacgccgtccttcacttcctggcgatcgcccattcagcagaagtaccttaaccatcg acgactttgagacgattcgccagcgcgtcccagtgttatgcgatttgaagccatcggggaagt atgtcaccgccgacctgcaccgtgctggcggcatcccgcaagtgatgaaaatgctcttaaat gccggcctgttgcatggtgactgcttaaccatcaccggggagactattgcagagcgcttacg ccacgtcccggataccccggatccgaatcaagacgtaatccgcccctttgaccaaccgttat atgccacagggcacctggccattctgaaaggaaacctggcatccgaaggggcggttgcta agatcagcggcgtgaagaatcctcaaattacggggccggcacgcgtattcgacagcgaag aggcatgcttggacgccatcttggctggcaaaattaaccctggtgacgttattgttattcgctac gaaggtccggtgggcggcccagggatgcgcgagatgctggccccacatctgccatcatt ggtgccgggttaggggatagtgttggactgattacagatgggcgcttttcgggtggtacttatg gtatggtggtgggccatgttgcaccggaagcggccgtgggtgaaccatcgcgcttgtccaa gagggcgactctattactatcgatgctcaccgccgtctgcttcagctgaatgtatcagaagag gagttagcggcgcgccgcgccaagtggcaaccaccggcccctcgctacactcgtggtgtttt ggcgaagtatgccaagctcgttagctcgagcagcttgggtgccgttacggaccgtttcgtg | 2 |
| B7 (L95I) nucleotide sequence | tggccgagaattggcgtagtcgtattattaccgagggcgtgcaacgtacgccgaatcgcgca atgctgcgtgcagttgggttcggtgacgaggacttcaacaagccgattgtcggcgtggccag cgcccactcgactattaccccttgtaatatggggattgcggcgttggcctcgcgtgccgaggc gggtattcgtgcggcgggtggtatgccgcaactgttcggaacgatcacagtctctgatggcat tagcatgggaaccgagggaatgaagtatattgtgagccgtgatgtcatcgctgatagca ttgagactgtttgtaacgcccagtctatggatggcgttttggcgatcggtggctgtgataagaac atgccgggagcgatgatcgcaatggcgcgtatgaatattccggcgattttcgtgtacggtggg accatcaagcctgggcattggcagggtcaggatttaactgtggtatccgcgttcgaggcagt gggtcaattcagcgcgggtaaaatggatgaagcgactctccacgcgattgagcaccacgc ctgccccggggcgggctcttgcggcggtatgttcacagctaacacgatgagttccgcattcg aggccatgggcatgtcgttgatgtatagctcgacaatgaccgccgaagacgcggagaagg ccgatagcaccgaactggctggtaaggtgctcgtggaagcgattcgtaagaatattcgtccc cgtgacattatcacgcgcaagtcaatcgaaaacgcaatctccgtgattatggctgtcggcggt tccaccaacgccgtccttcacttcctggcgatcgcccattcagcagaagtaccttaaccatcg acgactttgagacgattcgccagcgcgtcccagtgttatgcgatttgaagccatcggggaagt atgtcaccgccgacctgcaccgtgctggcggcatcccgcaagtgatgaaaatgctcttaaat gccggcctgttgcatggtgactgcttaaccatcaccggggagactattgcagagcgcttacg ccacgtcccggataccccggatccgaatcaagacgtaatccgcccctttgaccaaccgttat atgccacagggcacctggccattctgaaaggaaacctggcatccgaaggggcggttgcta | 3 |

TABLE 1-continued

| Name | Sequence: | SEQ ID NO: |
|---|---|---|
| | agatcagcggcgtgaagaatcctcaaattacggggccggcacgcgtattcgacagcgaag<br>aggcatgcttggacgccatcttggctggcaaaattaaccctggtgacgttattgttattcgctac<br>gaaggtccggtgggcggcccagggatgcgcgagatgctggccccacatctgccatcatt<br>ggtgccgggttaggggatagtgttggactgattacagatgggcgcttttcgggtggtacttatg<br>gtatggtggtgggccatgttgcaccggaagcggccgtgggtggaaccatcgcgcttgtccaa<br>gagggcgactctattactatcgatgctcaccgccgtctgcttcagctgaatgtatcagaagag<br>gagttagcggcgcgccgcgccaagtggcaaccaccggcccctcgctacactcgtggtgttt<br>ggcgaagtatgccaagctcgttagctcgagcagcttgggtgccgttacggaccgtttcgtg | |
| B7 (L95I) amino acid sequence | MAENWRSRIITEGVQRTPNRAMLRAVGFGDEDFNKPIVGVASAHSTITP<br>CNMGIAALASRAEAGIRAAGGMPQLFGTITVSDGISMGTEGMKYSIVSRD<br>VIADSIETVCNAQSMDGVLAIGGCDKNMPGAMIAMARMNIPAIFVYGGTI<br>KPGHWQGQDLTVVSAFEAVGQFSAGKMDEATLHAIEHHACPGAGSCG<br>GMFTANTMSSAFEAMGMSLMYSSTMTAEDAEKADSTELAGKVLVEAIR<br>KNIRPRDIITRKSIENAISVIMAVGGSTNAVLHFLAIAHSAEVPLTIDDFETIR<br>QRVPVLCDLKPSGKYVTADLHRAGGIPQVMKMLLNAGLLHGDCLTITGE<br>TIAERLRHVPDTPDPNQDVIRPFDQPLYATGHLAILKGNLASEGAVAKISG<br>VKNPQITGPARVFDSEEACLDAILAGKINPGDVIVIRYEGPVGGPGMREM<br>LAPTSAIIGAGLGDSVGLITDGRFSGGTYGMVVGHVAPEAAVGGTIALVQ<br>EGDSITIDAHRRLLQLNVSEEELAARRAKWQPPAPRYTRGVLAKYAKLV<br>SSSSLGAVTDRFV | 4 |
| G8 (V96F) nucleotide sequence | atggccgagaattggcgtagtcgtattattaccgagggcgtgcaacgtacgccgaatcgcgcaatgct<br>gcgtgcagttgggttcggtgacgaggacttcaacaagccgattgtcggcgtggccagcgcccactcg<br>actattacccccttgtaatatggggattgcggcgttggcctcgcgtgccgaggcgggtattcgtgcggcgg<br>gtggtatgccgcaactgttaggaacgatcacagtctctgatggcattagcatgggaaccgagggaatg<br>aagtatagtctgtttagccgtgatgtcatcgctgatagcattgagactgtttgtaacgcccagtctatggat<br>ggcgttttggcgatcggtggctgtgataagaacatgccgggagcgatgatcgcaatggcgcgtatgaa<br>tattccggcgattttcgtgtacggtgggaccatcaagcctgggcattggcagggtcaggatttaactgtg<br>gtatccgcgttcgaggcagtgggtcaattcagcgcgggtaaaatggatgaagcgactctccacgcgat<br>tgagcaccacgcctgcccccggggcgggctcttgcggcggtatgttcacagctaacacgatgagttccg<br>cattcgaggccatgggcatgtcgttgatgtatagctcgacaatgaccgccgaagacgcggagaaggc<br>cgatagcaccgaactggctggtaaggtgctcgtggaagcgattcgtaagaatattcgtcccccgtgacat<br>tatcacgcgcaagtcaatcgaaaacgcaatctccgtgattatggctgtcggcggttccaccaacgccgt<br>ccttcacttcctggcgatcgcccattcagcagaagtaccctttaaccatcgacgactttgagacgattcgc<br>cagcgcgtcccagtgttatgcgatttgaagccatcggggaagtatgtcaccgccgacctgcaccgtgct<br>ggcggcatcccgcaagtgatgaaaatgctcttaaatgccggcctgttgcatggtgactgcttaaccatc<br>accggggagactattgcagagcgcttacgccacgtcccggataccccggatccgaatcaagacgta<br>atccgcccdttgaccaaccgttatatgccacagggcacctggccattctgaaaggaaacctggcatc<br>cgaaggggcggttgctaagatcagcggcgtgaagaatcctcaaattacggggccggcacgcgtattc<br>gacagcgaagaggcatgcttggacgccatcttggctggcaaaattaaccctggtgacgttattgttattc<br>gctacgaaggtccggtgggcggcccagggatgcgcgagatgctggccccacatctgccatcattgg<br>tgccggttaggggatagtgttggactgattacagatgggcgcttttcgggtggtacttatggtatggtggt<br>gggccatgttgcaccggaagcggccgtgggtggaaccatcgcgcttgtccaagagggcgactctatt<br>actatcgatgctcaccgccgtctgcttcagctgaatgtatcagaagaggagttagcggcgcgccgcgc<br>caagtggcaaccaccggccctcgctacactcgtggtgttggcgaagtatgccaagctcgttagctc<br>gagcagcttgggtgccgttacggaccgtttcgtg | 5 |
| G8 (V96F) amino acid sequence | MAENWRSRIITEGVQRTPNRAMLRAVGFGDEDFNKPIVGVASAHSTITP<br>CNMGIAALASRAEAGIRAAGGMPQLFGTITVSDGISMGTEGMKYSLFSR<br>DVIADSIETVCNAQSMDGVLAIGGCDKNMPGAMIAMARMNIPAIFVYGGT<br>IKPGHWQGQDLTVVSAFEAVGQFSAGKMDEATLHAIEHHACPGAGSCG<br>GMFTANTMSSAFEAMGMSLMYSSTMTAEDAEKADSTELAGKVLVEAIR<br>KNIRPRDIITRKSIENAISVIMAVGGSTNAVLHFLAIAHSAEVPLTIDDFETIR<br>QRVPVLCDLKPSGKYVTADLHRAGGIPQVMKMLLNAGLLHGDCLTITGE<br>TIAERLRHVPDTPDPNQDVIRPFDQPLYATGHLAILKGNLASEGAVAKISG<br>VKNPQITGPARVFDSEEACLDAILAGKINPGDVIVIRYEGPVGGPGMREM<br>LAPTSAIIGAGLGDSVGLITDGRFSGGTYGMVVGHVAPEAAVGGTIALVQ<br>EGDSITIDAHRRLLQLNVSEEELAARRAKWQPPAPRYTRGVLAKYAKLV<br>SSSSLGAVTDRF | 6 |

The present invention features an isolated dehydratase enzyme (DHT) polypeptide comprising at least a single point mutation. In some embodiments, the point mutation increases specific activity of the DHT polypeptide compared to a wild type DHT protein. In some embodiments, the point mutation is L95I. In other embodiments, the point mutation is V96F.

The present invention may also feature an isolated dehydratase enzyme (DHT) polypeptide composition comprising a sequence that is at least 90% identical to SEQ ID NO: 4 or SEQ ID NO: 6 (Table 1).

In some embodiments, the dehydratase enzyme (DHT) polypeptide comprises a polypeptide that is at least 80% identical to SEQ ID NO: 4. In some embodiments, the DHT polypeptide comprises a polypeptide that is at least 85% identical to SEQ ID NO: 4. In some embodiments, the DHT polypeptide comprises a polypeptide that is at least 90% identical to SEQ ID NO: 4. In some embodiments, the DHT polypeptide comprises a polypeptide that is at least 93% identical to SEQ ID NO: 4. In some embodiments, the DHT polypeptide comprises a polypeptide that is at least 95% identical to SEQ ID NO: 4. In some embodiments, the DHT polypeptide comprises a polypeptide that is at least 96% identical to SEQ ID NO: 4. In some embodiments, the DHT polypeptide comprises a polypeptide that is at least 97% identical to SEQ ID NO: 4. In some embodiments, the DHT polypeptide comprises a polypeptide that is at least 98% identical to SEQ ID NO: 4. In some embodiments, the DHT polypeptide comprises a polypeptide that is at least 99% identical to SEQ ID NO: 4. In some embodiments, the DHT polypeptide comprises a polypeptide that is at least 99.5% identical to SEQ ID NO: 4. In some embodiments, the DHT polypeptide comprises a polypeptide that is at least 100% identical to SEQ ID NO: 4.

In some embodiments, the dehydratase enzyme (DHT) polypeptide comprises a polypeptide that is at least 80% identical to SEQ ID NO: 6. In some embodiments, the DHT polypeptide comprises a polypeptide that is at least 85% identical to SEQ ID NO: 6. In some embodiments, the DHT polypeptide comprises a polypeptide that is at least 90% identical to SEQ ID NO: 6. In some embodiments, the DHT polypeptide comprises a polypeptide that is at least 93% identical to SEQ ID NO: 6. In some embodiments, the DHT polypeptide comprises a polypeptide that is at least 95% identical to SEQ ID NO: 6. In some embodiments, the DHT polypeptide comprises a polypeptide that is at least 96% identical to SEQ ID NO: 6. In some embodiments, the DHT polypeptide comprises a polypeptide that is at least 97% identical to SEQ ID NO: 6. In some embodiments, the DHT polypeptide comprises a polypeptide that is at least 98% identical to SEQ ID NO: 6. In some embodiments, the DHT polypeptide comprises a polypeptide that is at least 99% identical to SEQ ID NO: 6. In some embodiments, the DHT polypeptide comprises a polypeptide that is at least 99.5% identical to SEQ ID NO: 6. In some embodiments, the DHT polypeptide comprises a polypeptide that is at least 100% identical to SEQ ID NO: 6.

In some embodiments, the DHT polypeptide described herein has no tag. In other embodiments, the DHT polypeptide described herein has no protein tag. In some embodiments, the DHT polypeptide described herein comprises a polyhistidine tag. In other embodiments, the DHT polypeptide described herein comprises a hexahistidine tag (HIS-tag). In some embodiments, the protein tag is placed at the N-terminus of the DHT polypeptide. In other embodiments, the protein tag is placed at the C-terminus of the DHT polypeptide.

In some embodiments, the protein tag is a HIS-tag. In other embodiments, the protein tag is a HA-tag. In some embodiments, the protein tag is a V5-tag. In other embodiments, the protein tag is a Strep-tag. In some embodiments, the protein tag is an MBP-tag. In other embodiments, the protein tag is a FLAG-tag.

In some embodiments, the DHT polypeptide described herein increases specific activity about 2-fold as compared to WT. In some embodiments, the DHT polypeptide increases specific activity about 3-fold as compared to WT. In some embodiments, the DHT polypeptide increases specific activity about 4-fold as compared to WT. In some embodiments, the DHT polypeptide increases specific activity about 5-fold as compared to WT. In some embodiments, the DHT polypeptide increases specific activity about 6-fold as compared to WT. In some embodiments, the DHT polypeptide increases specific activity about 7-fold as compared to WT. In some embodiments, the DHT polypeptide increases specific activity about 8-fold as compared to WT. In some embodiments, the DHT polypeptide increases specific activity about 9-fold as compared to WT. In some embodiments, the DHT polypeptide increases specific activity about 10-fold as compared to WT.

In some embodiments, the present invention may feature a composition comprising the DHT polypeptide as described herein and at least one additional component. In other embodiments, the present invention may feature a cell free composition comprising the DHT polypeptide as described herein and at least one additional component. In some embodiments, the additional component may comprise a substrate, a buffer, a cofactor, a detergent, a solvent, a gas, or a combination thereof.

In some embodiments, the present invention features a method of using the DHT polypeptide as described herein or a composition as described herein. In some embodiments, wherein the DHT polypeptide or composition is utilized to catalyze a reaction inside of a cell. In other embodiments, the DHT polypeptide or composition is utilized to catalyze a reaction outside of a cell or in a cell-free system.

In some embodiments, the DHT polypeptide described herein may be utilized inside of a cell. In other embodiments, the DHT polypeptide described herein may be utilized outside of a cell. In some embodiments, the DHT polypeptide described herein may be utilized in a cell-free system.

In some embodiments, the present invention features an isolated nucleic acid comprising a sequence that encodes a polypeptide with the amino acid sequence of SEQ ID NO: 4. In other embodiments, the present invention features an isolated nucleic acid comprising a sequence that encodes a polypeptide with the amino acid sequence of SEQ ID NO: 6.

In some embodiments, the present invention features an isolated nucleic acid comprising the nucleotide sequence of SEQ ID NO: 3 or SEQ ID NO: 5. In some embodiments, the isolated nucleic acid sequence comprises a nucleic acid sequence that is 80% identical to SEQ ID NO: 3 or SEQ ID NO: 5. In some embodiments, the isolated nucleic acid sequence comprises a nucleic acid sequence that is 85% identical to SEQ ID NO: 3 or SEQ ID NO: 5. In some embodiments, the isolated nucleic acid sequence comprises a nucleic acid sequence that is 90% identical to SEQ ID NO: 3 or SEQ ID NO: 5. In some embodiments, the isolated nucleic acid sequence comprises a nucleic acid sequence that is 93% identical to SEQ ID NO: 3 or SEQ ID NO: 5. In some embodiments, the isolated nucleic acid sequence comprises a nucleic acid sequence that is 95% identical to SEQ ID NO: 3 or SEQ ID NO: 5. In some embodiments, the isolated nucleic acid sequence comprises a nucleic acid sequence that is 96% identical to SEQ ID NO: 3 or SEQ ID NO: 5. In some embodiments, the isolated nucleic acid sequence comprises a nucleic acid sequence that is 97% identical to SEQ ID NO: 3 or SEQ ID NO: 5. In some embodiments, the isolated nucleic acid sequence comprises a nucleic acid sequence that is 98% identical to SEQ ID NO: 3 or SEQ ID NO: 5. In some embodiments, the isolated nucleic acid sequence comprises a nucleic acid sequence that is 99% identical to SEQ ID NO: 3 or SEQ ID NO: 5. In some embodiments, the isolated nucleic acid sequence comprises a nucleic acid sequence that is 99.5% identical to SEQ ID NO: 3 or SEQ ID NO: 5. In some embodiments, the isolated nucleic acid sequence comprises a nucleic acid sequence that is 100% identical to SEQ ID NO: 3 or SEQ ID NO: 5.

Example

The following is a non-limiting example of the present invention. It is to be understood that said example is not intended to limit the present invention in any way. Equivalents or substitutes are within the scope of the present invention.

Figure 1:
FIG. 1 shows the enzymatic steps needed to convert glycerol to pyruvate. ALDO, alditol oxidase, DHAD, dihydroxy acid dehydratase.
Figure 2:
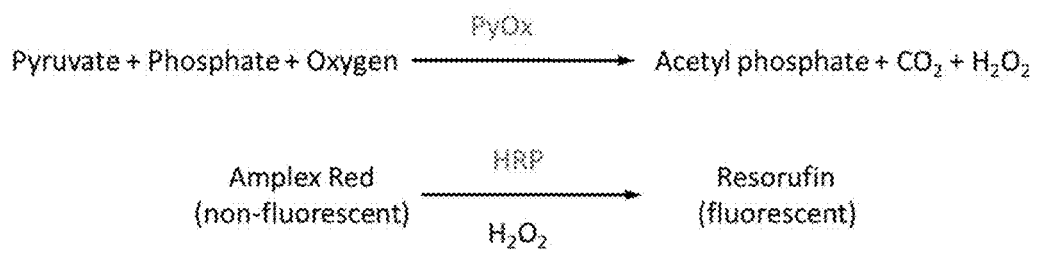
FIG. 2 shows the enzymatic steps used to convert pyruvate to the fluorescent dye resorufin.
Figure 3A:
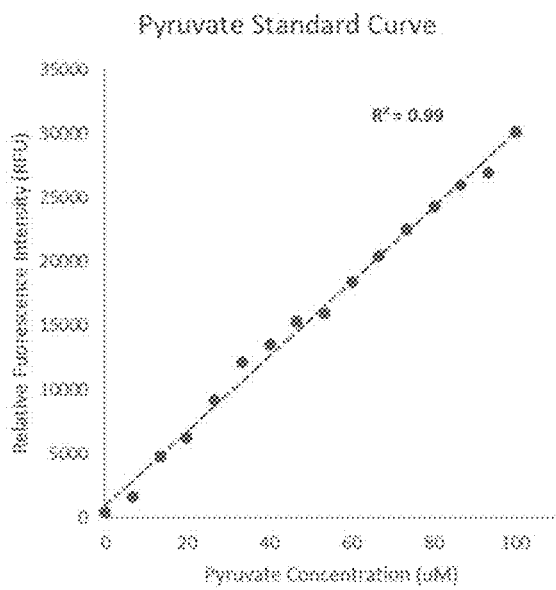
FIG. 3A shows a standard curve to calculate pyruvate concentration from fluorescence intensity data.
Figure 3B:
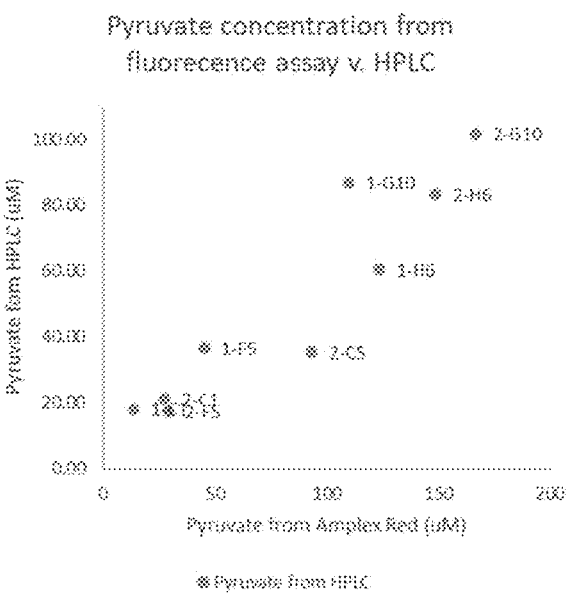
FIG. 3B shows a comparison of absolute pyruvate concentration values determined using the fluorescence assay vs. HPLC.

Establishing a fluorescence assay for measuring DHT activity. While multiple methods are available for pyruvate quantification, fluorescence assays provide a more sensitive method with a larger dynamic range. An enzymatic assay was selected that indirectly measures pyruvate concentration via hydrogen peroxide generation from the action of pyruvate oxidase (PyOx), with a fluorescence signal resulting from horseradish peroxidase (HRP)-mediated oxidation of Amplex Red (AR) (FIG. 2). After screening a range of values for concentrations of PyOx, HRP, and AR, a cocktail composition was produced (below) which allowed for reliable determination of pyruvate concentration in a microtiter plate and in presence of the assay buffer (250 mM HEPES). In this method, FIG. 3A shows that the pyruvate concentration could be determined down to 5 μM. Comparison of the pyruvate concentration measured using this assay vs. a well-defined HPLC method (below), for a representative set of variants, showed an acceptable agreement between the two methods in ranking of samples (Spearman correlation coefficient=0.78, FIG. 3B). This assay was thus used to screen variants in a high throughput screen.

Establishing an enzyme-linked immunosorbent assay (ELISA) for measuring protein concentrations: Analysis of screening data. After background subtraction, both ELISA and fluorescence signals were normalized within each plate to provide normalized expression ("NormELISA") and activity signals ("NormRFU"). Such normalization not only would enable plate-to-plate comparison (if necessary), but also would allow for the processing of the resulting data in a unified manner.

Multiple filters were applied to the NormELISA and NormRFU signals to remove outliers or noise. The signals from WT wells were used as a reference for hit picking. WT wells with NormELISA signal below 0.5 or NormRFU signal below 0.2 were removed from the sample pool in each plate. Variants with NormELISA below 20% of the WT or NormRFU below 50% of the WT were dropped. Dividing NormRFU by NormELISA then yields a quantity which is proportional to the specific activity of each variant, which is called ENS (for expression normalized signal). Therefore:

$$ENS_{variant\ i} = \frac{NormRFU_{variant\ i}}{NormELISA_{variant\ i}}$$

Wells that showed an ENS value greater than Median $(ENS_{WT})+2*StD\ (ENS_{WT})$, where StD is the standard deviation, were identified as hits and progressed into the next round of screening.

In the second round of screening, hits from the first round were arrayed into 96-well deep well plates similar to the first round, but with two main differences (1) Each variant was grown in duplicates and (2) sixteen WT wells were used in the plate, instead of the eight used in the primary screening. Data analysis and hit identification were done in the same way as described herein.

Figure 4A:
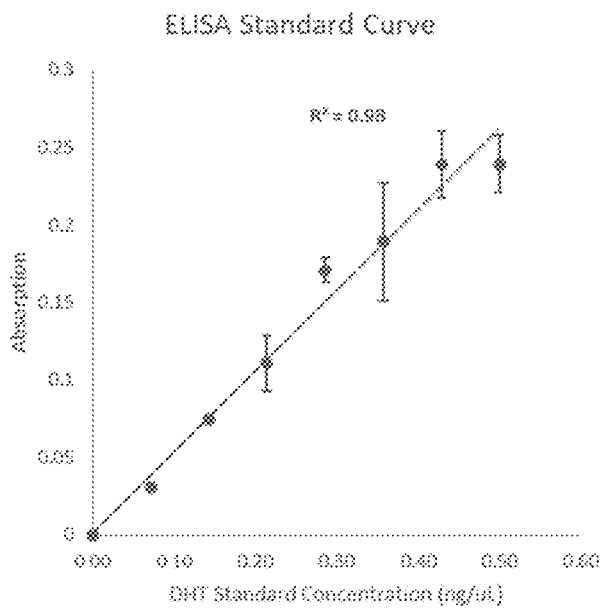
FIG. 4A shows an ELISA raw absorption reads vs. DHT standard concentration.
Figure 4B:
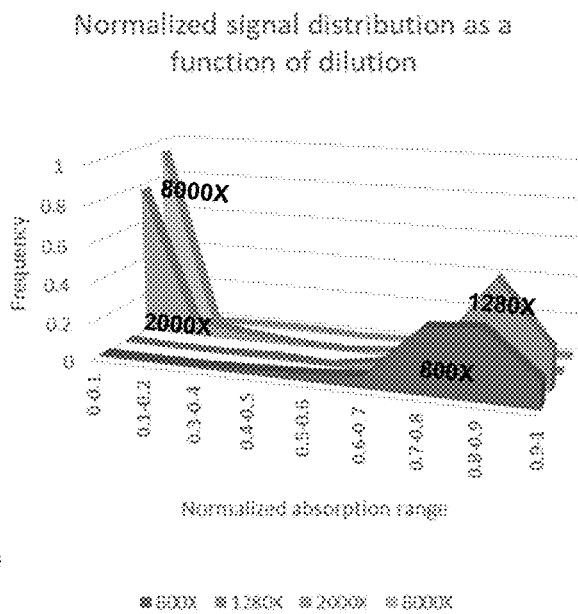
FIG. 4B shows a distribution of normalized ELISA reads vs. sample dilution for a representative plate of variants and WT (n=80).

A hexahistidine tag (HIS-tag) was incorporated at the N-terminus of the expressed DHT variants to enable immobilized metal affinity chromatography (IMAC) for purification of the protein of interest out of the bacterial lysate. Significant background noise in both activity and concentration determination assays were observed in preliminary tests, consistent with previous reports on difficulty of pyruvate concentration determination in bacterial lysates. Purifying the enzymes removed the endogenous pyruvate and proteins, hence simplifying downstream measurements. An ELISA was employed for quantifying the protein of interest after immobilized metal affinity chromatography (IMAC) purification. After screening different conditions for ELISA, a set of parameters was selected that would yield a linear standard curve for protein quantification (FIG. 4A). The background-subtracted signals showed an approximately 5-fold change and could be fit with a linear curve for transformation of absorption data into concentration using a DHT standard with defined concentration. To make sure that most of the ELISA reads in each plate fall within the dynamic range of the assay, the effect of variant dilution on the ELISA signal was probed. Here, FIG. 4B shows the distribution of ELISA signal after normalization to the maximum signal in each plate and subtraction of background, for a representative plate. Based on these results, two dilutions of 800× and 4000× were chosen to be used for each plate in the screen, to make sure that the most wells in the plate show an ELISA signal that is not oversaturated.

Design of the variant DHT library: DNA sequences. All DNA synthesis and cloning were done by Twist Biosciences. TvDHT WT backbone (WP_126985616.1, SEQ ID NO. 1) was codon optimized to use the highest frequency codon at each amino acid position, according to a *E. coli* codon utilization table. Synthesized genes were cloned into the pET28a(+) vector between the NdeI and XhoI sites, and therefore, containing an N-terminal HIS-tag. Nucleotide and amino acid sequences of TvDHT are described herein.

Library design. A 3D model of the TvDHT backbone was constructed using SwissModel and PDB 6OVT as the template. Heteroatoms were separately added to the model after alignment of the modeled structure with 6OVT. Active-site proximal residues were identified as those within 10 Å of the water oxygen molecule at the center of the active site and were included in Library-B. Residues that were thought to be important were identified and included in Library-A. The 15 DHT sequences from Sutiono et al. were aligned using PRALINE. Alignments were converted to a position specific scoring matrix (PSSM) using PSI-BLAST. A custom Python script was written to convert the PSSM into an Excel sheet listing all positions along the protein sequence and the allowed amino acids (AAs) under the following conditions: For each position in Library-A, AAs with a log-likelihood smaller than zero were removed from the pool. This favors AAs that were either observed in the alignment or were frequently observed at random in nature. WT amino acids were removed from the pool along with strictly conserved ones (only one AA observed in the alignment). Residues shared between the two libraries were pushed to Library-B, yielding a final count of 40 AAs in library A and 48 AAs in library B The starting point for backbone selection and library generation was a set of 15 DHT naturally occurring sequences reported by Sutiono et al. (Sutiono, S.; Teshima, M.; Beer, B.; Schenk, G.; Sieber, V. Enabling the Direct Enzymatic Dehydration of D-Glycerate to Pyruvate as the Key Step in Synthetic Enzyme Cascades Used in the Cell-Free Production of Fine Chemicals. ACS Catal. 2020. —Table 51 of the corresponding reference). TvDHT was chosen as the starting sequence (SEQ. ID. NO. 1) (hereafter "WT" or "WT backbone") due to its high thermostability. A site saturation library (SSL) was generated based on the WT backbone with a reduced amino acid (AA) alphabet, wherein AA changes were introduced according to an alignment of the 15 backbones discussed above. The targeted positions were further narrowed down by focusing the library onto regions of the protein that were thought to be important for activity of homologous enzymes based on literature data. This included the N-terminal region suggested to be important in substrate recognition, a helix-loop-helix region capping the active site and shown to go through a conformational change to allow for substrate binding and finally a helical turn which forms part of the active and is of different lengths among various homologs. Mutations at 48 AA positions were yielded with the approach described here, which were screened for activity as discussed below.

Identifying improved variants: DNA transformation. WT and variant plasmids were transformed into Rosetta (DE3) chemically competent cells (Novagen). Briefly, 50 ng of plasmid was added to a thin-walled PCR tube (Genesee Scientific) containing 5 µL of ice-chilled competent cells and kept on ice for 5 minutes. Cells were then heat-shocked at 42° C. for 30 seconds in a water batch and then kept on ice for 5 minutes. After the addition of 100 µL of SOC (super optimal broth) media, cells were incubated at 37° C. for 1 hour. All the tube contents were then plated onto LB-Kanamycin plates containing 50 µg/mL of Kanamycin sulfate and incubated at 37° C. overnight. Plates were collected the next day and stored for later steps (below).

Colony picking. Enough colonies were picked for each position in the library to have at least 63% coverage of the library diversity at that position. This approach has been suggested to have a 95% chance of theoretically yielding one of the top three performers in a library. Colonies were attempted to be picked in multiples of 8, to simplify manual colony picking into 96-well plates. Therefore, depending on the diversity at each position, the number of clones to pick for 63% coverage was calculated using GLUE and then rounded up to the nearest multiple of 8, to determine how many colonies should be picked at each AA position. This approach resulted in a predetermined plate map of where library variants on each 96-well plate will be. WT clones were picked similarly. 96-well deep well plates (DWPs) were filled with 500 µL of Overnight Express Autoinduction media (Novagen) supplemented with 100 µg/mL of Kanamycin sulfate. Each plate contained 80 variants and 8 WT clones, leaving the last two columns empty for controls and standards. Plates were covered with breathable seals and incubated on a plate shaker at 700 rpm and 37° C. for 16 hours. Following overnight growth, glycerol stocks of the plates were made by adding 60 µL of the culture to 15 µL of 75% glycerol. Glycerol stocks were stored in −80° C. for later use. After measuring ODs, the left-over cultures were processed further in the screening pipeline (below).

High-throughput screening of variants. All pipetting operations in the screen were performed on a Biomek FX automated liquid handler. Following overnight growth in autoinduction media (see above) cultures were spun down at 3000 G and 4° C. for 15 minutes and supernatant was discarded. Pellets were frozen at −80° C. for 20 minutes, followed by room temperature incubation for 20 minutes, and were then resuspended in 100 µL of BPER complete (complete bacterial protein extraction reagent; Thermo Fisher Scientific). The suspension was incubated at room temperature for 1 hour, after which the plates were centrifuged for 15 minutes at 3000 G and 4° C. The soluble lysate was removed and added to 20 µL of 50% IMAC resin slurry (Genesee Scientific) in storage buffer (100 mM HEPES pH 7.5, 500 mM NaCl). After pipetting the suspension up and down 160 times, the plates were spun down for 3 minutes at 1000 G and the supernatant was removed and collected as flow through. 100 µL of wash buffer (100 mM HEPES pH 7.5, 500 mM NaCl, 10 mM imidazole) was added and pipetted up and down 64 times. The plates were spun down as before, and the supernatant was discarded. This wash step was repeated twice. Following the last wash, 100 µL of elution buffer (100 mM HEPES pH 7.5, 500 mM NaCl, 200 mM imidazole) was added to each well and pipetted up and down 160 times. Plates were spun down again and the supernatant containing purified enzyme was transferred to an AcroPrep Advance filter plate (10K NMWCO, Pall Corporation). Following the addition of 150 µL of storage buffer the plate was centrifuged for 20 minutes at 3000 G and 4° C. and the flow through was discarded. This buffer exchange process was repeated two more times, with the last spin going for 10 minutes. The final buffer exchanged product was stored at 4° C. overnight and used in enzymatic reactions or diluted and used to coat ELISA plates on the same day (see below).

For 24-well plate scale expressions, 2 mL of the growth media was transferred to each well of a 24-well Whatman round bottom deep well plate (Sigma Aldrich) and each well was inoculated with either 2 µL of cell suspensions from glycerol stocks or a freshly streaked colony. Plates were sealed with a breathable film and incubated at 30° C. for 16 hours at 250 rpm in a floor incubator shaker. Following overnight incubation, cultures were processed similar to 96-well plates cultures.

Large scale protein expression and purification. Cells were grown in TB media supplemented with 50 µg/mL kanamycin sulfate at 37° C. and 200 rpm until A600=0.6. Cultures were cooled to 18° C. and expression was induced by addition of IPTG (Isopropyl β-d-1-thiogalactopyranoside). Following overnight growth, cell pellets were collected by centrifugation, frozen, and then resuspended in 5 mL lysis buffer (50 mM Tris pH 8.0, 300 mM NaCl, 5% glycerol, 1 mM PMSF) per gram of cell paste. Cell lysates were prepared by sonication and cellular debris was removed by centrifugation. Clarified lysate was loaded onto GE XK series columns containing IMAC-Nickel resin. Proteins were eluted using a 15CV gradient from buffer A (50 mM Tris pH 8.0, 300 mM NaCl, 10% glycerol) into 70% buffer B (2 M imidazole, 50 mM Tris pH 8.0, 300 mM NaCl, 10% glycerol). Fractions containing proteins of interest were pooled and transitioned into buffer A (above) with a GE HiPrep 26/10 desalting column.

Protein quantification. For ELISA, two dilutions (800× and 4000×) of the purified proteins were selected for use in the screen after testing a range of dilutions. 60 µL of diluted samples and standards were added to flat-bottom 96-well Immunograde plates (Genesee Scientific) and incubated overnight at 4° C. Plates were washed on a Biotek ELx405 automated plate washer with PBS+0.1% Tween-20. 60 µL of 5000× diluted mouse anti-HIS antibody (Genscript Cat. No. A00186) in the blocking solution (PBS+0.1% Tween-20+ 0.5% BSA) was added to plates afterwards. Plates were incubated for an hour at room temperature, followed by another wash and hour-long incubation with 5000× diluted horseradish peroxidase (HRP)-conjugated goat anti-mouse antibody (Genesee Scientific Cat. No. 20-304). 60 µL of 1-step Ultra TMB was added to washed plates and incubated for 20 minutes. The reactions were stopped via addition of 60 µL of 3% HCl and absorption was measured at 485 and 560 nm. $A_{485}$-$A_{560}$ was used as the raw ELISA signal.

To construct a standard curve, WT TvDHT previously expressed and purified in the lab and quantified by the Bicinchoninic acid (BCA) assay was used. For protein quantification in larger scale expressions, a commercially available HIS-tagged CD64 protein (Thermo Fisher Scientific) was used as the standard since the follow up experiments showed that BCA assay was not a reliable method to measure protein concentrations, possibly due to the presence of the iron-sulfur cluster in the particular enzyme studied here. Nevertheless, since standard curves are only used in their linear range and act as just a linear transformation of data, the relative values of protein concentrations determined using either of the protein standards should hold.

DHT variants were put onto 96-well plates for growth and screening. Each plate contained both the variants and wild-type (VVT) DHT clones. In this way, activity and expression data could be directly compared between variants and multiple replicas of WT. The proteins were purified from the lysates using the HIS-tag handle since the initial screening attempts resulted in false positives, i.e., primary hits that did not perform as expected in follow up experiments. Since the goal was to identify variants with improved specific activity, i.e., activity per unit of enzyme mass, both the activity and expression level of each clone were measured. Therefore, noise from any of these measurements could contribute to noise in the final signal derived from them. Previous efforts using just activity to identify improved DHT variants faced difficulty in measuring pyruvate levels in lysates, due to the presence of endogenous proteins, and possibly, endogenous pyruvate. Preliminary ELISA experiments using lysate showed a low signal to noise ratio (data not shown). Both observations led to the consideration of IMAC-assisted purification of variants in the screen. While IMAC performance was not perfect in that the lysate was not always completely depleted from the protein of interest, and performance was not even among different variants, it allowed for reduced background noise in both the assay and ELISA.

After applying various transformations and filters to the data, hits as variants were identified which showed ENS (expression normalized signal) two standard deviations above WT median signal. A graphical representation of the processed data for a representative set of samples is shown in FIG. 5. Here, the normalized activity signal against the normalized protein expression signal was plotted (at 800× sample dilution) for both the variants (open circles) and WT (closed circles). Width of each circle is proportional to the corresponding ENS signal. The shaded area shows an approximate region where data filters would reject samples. Since filters are applied across each individual plate, different thresholds are used for different plates. Because of this, the shaded region approximates the rejected region, and some hits may be identified inside it. Samples with very low ELISA signal yield large ENS values due to the division operation involved in calculating ENS and were rejected by the filters. Samples with higher expression yield higher activity, which is demonstrated by many of the WT samples in the top right section of FIG. 5. Improved mutants are hypothesized to be seen in the upper left corner of the above graph: samples that show activity as good as WT, but with less enzyme. Some of the variants satisfying this criterion and identified by the hit picking algorithm are labeled in FIG. 5. The same approach was used for a second round of screening which pruned the candidates further and yielded a pool of 16 candidates to analyze. These latter variants were expressed at a larger scale (24 well deep well plates; above) and processed similarly but analyzed manually. The raw fluorescence signal (in RFUs) was normalized to the protein concentrations calculated from the average of maximum two different dilutions (provided that both dilutions yielded signals within the range of the standard curve). In FIG. 6 the normalized activity data has been plotted for different variants and identified those better than WT by squares, i.e., those that are two standard deviations above the WT median. Note that A03G8 appears twice in the list, as it was picked up twice in the previous round and hence, was tested in two separate wells.

This last set of variants were expressed and purified in multiple wells of a 24-well deep well plate and pooled the wells to generate more material for activity measurements using HPLC. Product concentrations were measured after 5 hours using HPLC and protein concentrations were measured using enzyme linked immunosorbent assay (ELISA). Specific activity was measured via normalizing the product yield by the amount of enzyme present in the reaction (FIG. 7). These results suggest that two of the variants (G8 and B7) show specific activity that is almost 5-fold that of the WT enzyme.

Characterization of improved variants: Enzyme activity measurement. Preliminary studies suggested that a 5-hour reaction is suitable to avoid reaction saturation and yield detectable pyruvate in both HPLC and plate-based assays. 30 µL of enzyme sample was added to 30 µL of substrate solution (500 mM HEPES pH 7.5, 5 mM $MgCl_2$, 2 mM glycerate) and the mixture was incubated for 5 hours at 50° C.

For high-throughput screening, a fluorescence-based pyruvate assay was used. After optimizing different parameters (enzyme types, concentrations, buffers, and ionic strengths) to achieve a broad dose response to pyruvate concentration, the following composition was used: 250 mM HEPES pH 7.5, 2.5 mM $MgCl_2$, 0.2 mM thiamine pyrophosphate, 10 µM flavin adenine dinucleotide (FAD), 6 U/mL of pyruvate oxidase from *Aerococcus viridans* (AG Scientific), 3 U/mL of horseradish peroxidase (Thermo Scientific) and 100 µM of Amplex Red (Thermo Scientific). Following the enzymatic reaction, 30 µL of the detection cocktail was added to 30 µL of the reaction mixture and incubated at room temperature for 20 minutes. Fluorescence signal was measured on a TECAN Ultra plate reader at 535 nm (Exc)/595 nm (Emm).

For larger scale enzyme expressions, and to validate the fluorescence assay results, high performance liquid chromatography (HPLC) was used. An Agilent 1200 HPLC was equipped with a 30 cm Aminex HPX-87H column and a micro-guard cation H-refill cartridge. The column was heated to 55° C. and the sample block was maintained at 4° C. For each sample, 10 µL was injected and an isocratic mobile phase comprised of 100% sulfuric acid (10 mM) was used. The sample run time was a total of 45 minutes with glyceric acid eluting at 17.2 minutes, and pyruvate eluting at 16.1 minutes. For detection, a RID detector (Agilent) was used after a 2-hour equilibration period produced a stable baseline.

Sequencing. The mutations giving rise to activity improvement were established after sequencing 4 clones of each of the G8 and B7 variants. Glycerol stocks of each variant were plated onto LB-Kanamycin and single colonies were picked and inoculated into LB-Kanamycin. Plasmid DNA was prepared from overnight cultures using the ZymoPURE plasmid preparation kit (Zymo Research). Sanger sequencing service was provided by BATJ (San Diego, CA) using standard T7 primers (TAATACGACT-CACTATAGGG—SEQ ID NO: 7).

To better understand the time-dependence of activity in the new variants compared to WT, the produced pyruvate content was measured at different time-points using HPLC and normalized to the enzyme amount determined via ELISA. A larger batch expression of all three proteins (G8, B7, and WT) was used to allow for more downstream characterization, and to ensure that the above results were reproducible both in terms of specific activity and scalability of protein production for the future needs (see above). FIG. 8 shows that both G8 and B7 variants again show improved activity compared to WT, although the magnitude of improvement is reduced for B7 compared to the data presented above. Nonetheless, these results provide evidence that both variants show improved specific activities.

Four individual clones were sequenced from the glycerol stocks of each of the two improved variants. All four replicas in each variant showed the same coding region sequence. Each variant showed a single amino acid mutation at the expected position based on the library design. The B7 variant contained the mutation L95I and the G8 mutant contained V96F. These sequential mutations occur in proximity to the C-terminus in the homology model in the PDB, and on a loop which shows insertions and deletions in various homologs. While by design they are spatially close to the active site, they are not directly involved in substrate binding. Importantly, neither mutation is present in the pool of AA's observed in the sequence alignment used to generate the PSSM, which lends support to the decision to allow some randomness in the PSSM-based diversification introduced in the library.

In conclusion, the present invention utilized a highly stable DHT backbone to generate two new single point mutations that show a 2-5-fold increase in specific activity compared to WT. None of the discovered mutations are present in the pool of natural backbones reported by Sutiono et al. In addition to the focused library reported here, a full SSL library of all active-site proximal residues was generated which are currently in the process of being screened (data not shown). Altogether, the two libraries span 96 amino acid positions, and 1176 planned individual clones from which only 400 clones (34%) have been screened and reported.

In conclusion, the present invention was able to utilize a highly stable DHT backbone to generate two new single point mutations that show a 2-5-fold increase in specific activity compared to WT. None of the discovered mutations are present in the pool of natural backbones previously reported.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

EMBODIMENTS

The following embodiments are intended to be illustrative only and not to be limiting in any way.

Embodiment 1: An isolated dehydratase enzyme (DHT) polypeptide comprising at least a single point mutation, wherein the point mutation increases specific activity of the DHT polypeptide compared to a wild type DHT protein.

Embodiment 2: The isolated polypeptide of Embodiment 1, wherein the point mutation is L95I.

Embodiment 3: The isolated polypeptide of Embodiment 1 or Embodiment 2, where in the isolated DHT polypeptide comprises SEQ ID NO: 4.

Embodiment 4: The isolated polypeptide of any one of Embodiment 3, wherein the isolated DHT polypeptide comprising a sequence that is at least 90%, 93%, 95%, 97%, 98%, or 99% identical to SEQ ID NO: 4:

Embodiment 5: The isolated polypeptide of Embodiment 1, wherein the point mutation is V96F.

Embodiment 6: The isolated polypeptide of Embodiment 1 or Embodiment 5, where in the isolated DHT polypeptide comprises SEQ ID NO: 6.

Embodiment 7: The isolated polypeptide of Embodiment 2, wherein the isolated DHT polypeptide comprising a sequence that is at least 90%, 93%, 95%, 97%, 98%, or 99% identical to SEQ ID NO: 6.

Embodiment 8: The isolated polypeptide of any one of Embodiments 1-7, further comprising a protein tag.

Embodiment 9: The isolated polypeptide of any one of Embodiments 1-8, wherein the protein tag is a hexahistidine tag (HIS-tag).

Embodiment 10: A composition comprising the DHT polypeptide according to any one of Embodiments 1-9 and at least one additional component.

Embodiment 11: A cell free composition comprising the DHT polypeptide according to any one of Embodiments 1-9 and at least one additional component.

Embodiment 12: The composition of Embodiment 10 or Embodiment 11, wherein the additional component is a substrate, a buffer, a cofactor, a detergent, a solvent, a gas, or a combination thereof.

Embodiment 13: A method of using the DHT polypeptide according to any one of Embodiments 1-9 or composition according to Embodiment 10, wherein the DHT polypeptide or composition is utilized to catalyze a reaction inside of a cell Embodiment 14: A method of using the DHT polypeptide according to any one of Embodiments 1-9 or composition according to Embodiment 10 or Embodiment 11, wherein the DHT polypeptide or composition is utilized to catalyze a reaction outside of a cell or in a cell-free system Embodiment 15: An isolated dehydratase enzyme (DHT) polypeptide comprising a sequence that is at least 90% identical to SEQ ID NO: 4.

Embodiment 16: The isolated polypeptide of Embodiment 15, wherein the isolated DHT polypeptide is at least 93%, 95%, 97%, 98%, or 99% identical to SEQ ID NO: 4.

Embodiment 17: An isolated dehydratase enzyme (DHT) polypeptide comprising a sequence that is at least 90% identical to SEQ ID NO: 6.

Embodiment 19: The isolated polypeptide of Embodiment 17, wherein the isolated DHT polypeptide is at least 93%, 95%, 97%, 98%, or 99% identical to SEQ ID NO: 6.

Embodiment 20: The isolated polypeptide of any one of Embodiments 15-19, wherein the isolated DHT polypeptide has an increased specific activity as compared to a wild type DHT protein.

Embodiment 21: The isolated polypeptide of any one of Embodiments 15-20, further comprising a protein tag.

Embodiment 22: The isolated polypeptide of any one of Embodiments 15-21, wherein the protein tag is a hexahistidine tag (HIS-tag).

Embodiment 23: A composition comprising the isolated DHT polypeptide according to any one of Embodiments 15-22 and at least one additional component.

Embodiment 24: A cell-free composition comprising the isolated DHT polypeptide according to any one of Embodiments 15-22 and at least one additional component of the cell-free composition.

Embodiment 25: The composition of Embodiment 23 or Embodiment 24, wherein the additional component is a substrate, a buffer, a cofactor, a detergent, a solvent, a gas, or a combination thereof.

Embodiment 26: A method of using the isolated DHT polypeptide according to any one of Embodiments 15-22, or the composition according to Embodiment 24, wherein the isolated DHT polypeptide or composition is utilized to catalyze a reaction inside of a cell.

Embodiment 27: A method of using the isolated DHT polypeptide according to any one of Embodiments 15-22, or the composition according to Embodiment 24 or Embodiment 25, wherein the isolated DHT polypeptide or composition is utilized to catalyze a reaction outside of a cell or in a cell-free system.

What is claimed is:

1. An isolated dehydratase enzyme (DHT) polypeptide comprising at least a single point mutation, wherein the single point mutations are L95I or V96F and the isolated DHT polypeptide comprises a sequence that is at least 90% identical to SEQ ID NO: 4 or SEQ ID NO: 6.

2. The isolated polypeptide of claim 1, where in the isolated DHT polypeptide comprises SEQ ID NO: 4 or SEQ ID NO: 6.

3. The isolated polypeptide of claim 1, wherein the isolated DHT polypeptide comprises a sequence that is at least 95% identical to SEQ ID NO: 4 or SEQ ID NO: 6.

4. The isolated polypeptide of claim 1, further comprising a protein tag.

5. A composition comprising the DHT polypeptide according to claim 1, and at least one additional component.

6. The composition of claim 5, wherein the additional component is a substrate, a buffer, a cofactor, a detergent, a solvent, a gas, or a combination thereof.

7. A cell free composition comprising the DHT polypeptide according to claim 1, and at least one additional component.

8. The composition of claim 7, wherein the additional component is a substrate, a buffer, a cofactor, a detergent, a solvent, a gas, or a combination thereof.

9. A method of producing pyruvic acid or pyruvate, the method comprising: expressing the DHT polypeptide comprising at least a single point mutation, wherein the single point mutations are L95I or V96F, and the DHT polypeptide comprises a sequence that is at least 90% identical to SEQ ID NO: 4 or SEQ ID NO: 6.

10. A method of producing pyruvic acid or pyruvate, the method comprising providing a composition comprising a DHT polypeptide comprising at least one single point mutation, wherein the single point mutations are L95I or V96F and the DHT polypeptide comprises a sequence that is at least 90% identical to SEQ ID NO: 4 or SEQ ID NO: 6, in a cell-free medium, and a composition comprising glycerol or glycerate.

11. The isolated DHT polypeptide of claim 1, wherein the isolated DHT polypeptide has an increased specific activity as compared to a wild type DHT protein.

12. The method of claim 10, wherein the DHT polypeptide further comprises a protein tag.

13. The method of claim 10, wherein the composition comprises at least one additional component.

14. The method of claim 13, wherein the additional component is a substrate, a buffer, a cofactor, a detergent, a solvent, a gas, or a combination thereof.

15. A method of using the isolated DHT polypeptide according claim 1, wherein the isolated DHT polypeptide or composition is utilized to catalyze a reaction outside of a cell or in a cell-free system.

16. The method of claim 14, wherein the substrate is glycerol or glycerate.

17. The method of claim 9, wherein the DHT polypeptide catalyzes the conversion of glycerol or glycerate to pyruvic acid or pyruvate.

\* \* \* \* \*